US009216940B2

(12) United States Patent
Curtis et al.

(10) Patent No.: US 9,216,940 B2
(45) Date of Patent: Dec. 22, 2015

(54) POLYOL SYNTHESIS FROM FATTY ACIDS AND OILS (75) Inventors: Jonathan Curtis, Edmonton (CA); Guoguang Liu, Edmonton (CA); Tolibjon Omonov, Edmonton (CA); Ereddad Kharraz, Edmonton (CA)

(73) Assignee: THE GOVERNORS OF THE UNIVERSITY OF ALBERTA, Edmonton, Alberta (CA)

( * ) Notice: Subject to any disclaimer, the term of this patent is extended or adjusted under 35 U.S.C. 154(b) by 225 days.

(21) Appl. No.: 13/811,362

(22) PCT Filed: Jul. 21, 2011

(86) PCT No.: PCT/CA2011/000843
§ 371 (c)(1),
(2), (4) Date: May 8, 2013

(87) PCT Pub. No.: WO2012/009801
PCT Pub. Date: Jan. 26, 2012

(65) Prior Publication Data
US 2013/0274494 A1 Oct. 17, 2013

Related U.S. Application Data (60) Provisional application No. 61/366,416, filed on Jul. 21, 2010.

(51) Int. Cl.
C09F 7/00 (2006.01)
C07C 67/08 (2006.01)
C07C 67/31 (2006.01)
(Continued)

(52) U.S. Cl.
CPC .............. *C07C 67/08* (2013.01); *C07C 67/31* (2013.01); *C08G 18/36* (2013.01); *C11C 3/00* (2013.01); *C11C 3/003* (2013.01); *C11C 3/006* (2013.01)

(58) Field of Classification Search
CPC ..................................................... C07C 67/347
USPC ............................................................. 554/25
See application file for complete search history.

(56) References Cited

U.S. PATENT DOCUMENTS

2007/0110877 A1* 5/2007 Kassim Shaari et al. ..... 426/611
2008/0293913 A1* 11/2008 Abu Hassan et al. ......... 528/361
2010/0190951 A1* 7/2010 Suppes et al. .................. 528/85

FOREIGN PATENT DOCUMENTS

CN 101314632 12/2008
CN 101314632 A * 12/2008
(Continued)

OTHER PUBLICATIONS

Lozada et al., Journal of Applied Polymer Science, 2009, 113,2552-2560.*

(Continued)

Primary Examiner — Deborah D Carr
(74) Attorney, Agent, or Firm — Bennett Jones LLP (57) ABSTRACT A method for preparing polyols from fatty acid substrates such as free fatty acids, alkyl esters of fatty acids, monoglycerides, diglycerides, and triglycerides. The method comprises the steps of (a) epoxidizing an unsaturated fatty acid substrate and (b) hydroxylating the epoxidized fatty acid substrate with at least one diol to produce a polyol or a blend of polyols. The method may be varied to produce polyols with desired functionality, molecular weights, or viscosity.

18 Claims, 7 Drawing Sheets

GPC graph of canola oil polyol (51) Int. Cl.
*C11C 3/00* (2006.01)
*C08G 18/36* (2006.01)

(56) References Cited

FOREIGN PATENT DOCUMENTS

| CN | 200810132276 | | 12/2008 |
|---|---|---|---|
| GB | 1100404 | | 1/1968 |
| GB | 1100404 A | * | 1/1968 |
| WO | 9421702 | | 9/1994 |
| WO | WO 9421702 A1 | * | 9/1994 |
| WO | 0005317 | | 2/2000 |
| WO | WO 0005317 A1 | * | 2/2000 |
| WO | 2012009801 | | 1/2012 |

OTHER PUBLICATIONS

Pielichowski et al., Polimery, 2005, 50(10), 723-727.*
Lozada, Z. et al.; Soy-Based Polyols from Oxirane Ring Opening by Alcoholysis Reaction; Journal of Applied Polymer Science; 2009; vol. 113; pp. 2552-2560.
Pielichowski, J. et al.; Polimery; 2005; vol. 50, No. 10; pp. 723-727.

* cited by examiner

Peak group D: *m/z*: 433  and its isomer

*m/z*: 447

*m/z*: 475

*m/z*: 315 is from saturated C16 FFAs

*m/z*: 297=315-18

Peak group C: *m/z*:789=433+357-1

*m/z*=730, 820

Peak group B:

*m/z*:1162    *m/z*:1086

*m/z*:1176

Peak group B: there are some molecular ions 1443, 1519, 1800, 1815 and 1873.

Peak group A: number average molecualr weight of this peak is around 3100.

POLYOL SYNTHESIS FROM FATTY ACIDS AND OILS

RELATED APPLICATION

This application claims the benefit of and is National Phase Entry of International Application Number PCT/CA2011/000843 filed Jul. 21, 2011, and claims the benefit of U.S. Provisional Patent Application No. 61/366,146 filed Jul. 21, 2010, which is hereby incorporated by reference in its entirety.

FIELD OF THE INVENTION

The present invention relates to a process for the preparation of polyols from fatty acid substrates such as vegetable oils.

BACKGROUND OF THE INVENTION

In polymer chemistry, polyols are compounds with multiple hydroxyl functional groups available for chemical reactions. A major use of polyols is as a reactant to make polymers. Polyols may also be used for other purposes including in cosmetic formulations, lubricants and as chemical intermediates. Polyols themselves may be monomeric, oligomeric or polymeric. The ability to produce polyols of different molecular weights is desirable since these can be used to produce polymer networks with different properties. Monomeric or oligomeric polyols may be polymerized, for example into polyesters or polyethers, before conversion to other polymers such as polyurethanes.

Polyol production from renewable, non-petroleum based sources is desirable from a sustainability perspective. Methods are known for the preparation of polyols from vegetable oil. Known methods for the preparation of polyols often involve harsh reaction conditions that are not easily controlled, and typically involve expensive starting materials and catalysts.

There is a need in the art for an alternative method of producing polyols from a sustainable source. Furthermore, it would be desirable to have a process which may be easily varied to provide polyols with a desired functionality.

SUMMARY OF THE INVENTION

In one aspect, the invention comprises a method for the preparation of polyols from a fatty acid substrate having at least one C—C double bond, comprising the steps of:
  (a) epoxidizing the fatty acid substrate with an acid and an oxidizing agent to obtain an epoxidized fatty acid substrate; and
  (b) hydroxylating the epoxidized fatty acid substrate with an alkane diol and a mineral acid to obtain a polyol.

The fatty acid substrate may comprise a free fatty acid, such as oleic acid, an alkyl ester of a fatty acid, a monoglyceride, a diglyceride, or a triglyceride, or mixtures thereof. The triglyceride may comprise an unsaturated vegetable oil, such as canola oil, olive oil, sunflower oil, corn oil, soy oil, flax oil, palm oil or other naturally sourced plant oils. Unsaturated triglycerides may also be sourced from certain animal oil sources such as tallow or fish oils.

In one embodiment, the oxidizing agent comprises hydrogen peroxide. In one embodiment, the alkane diol comprises 1,3-propanediol, or 1,2 propanediol, or mixtures thereof. In another embodiment, the mineral acid comprises sulphuric acid.

Reaction methods and conditions may be varied for the hydroxylation of the epoxidized fatty acid substrate, with the goal of producing polyols with a desirable balance between hydroxyl content and viscosity, for the production of polymers, such as polyurethanes. Therefore, in another aspect, the invention may comprise a method of producing a blend of polyols having a desired average molecular weight, viscosity or hydroxyl number, comprising the steps of:
  (a) epoxidizing an unsaturated fatty acid substrate; and
  (b) hydroxylating the epoxidized fatty acid substrate with two or more reactive alcohols, at least one of which is a diol, to produce two or more polyols.

In one embodiment, the epoxidation step is stopped prior to complete epoxidation of the unsaturated fatty acid substrate, resulting in a blend of polyols having a lower viscosity or lower average molecular weight.

In another embodiment, the at least one diol comprises 1,2 propanediol, or 1,3 propanediol, or mixtures thereof. The ratio of 1,2 propanediol to 1,3 propanediol may be controlled to produce a blend of polyols with desired properties. In another embodiment, one reactive alcohol comprises ethanol and the ratio of ethanol to diol is controlled to produce a blend of polyols having greater viscosity or greater hydroxyl number as the relative amount of ethanol decreases.

In another embodiment, the fatty acid substrate is blended from different fatty acid substrates in order to produce a blend of polyols having a desired property.

BRIEF DESCRIPTION OF THE DRAWINGS

The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows.

DETAILED DESCRIPTION OF PREFERRED EMBODIMENTS

The invention relates to the preparation of polyols. When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

Figure 1:
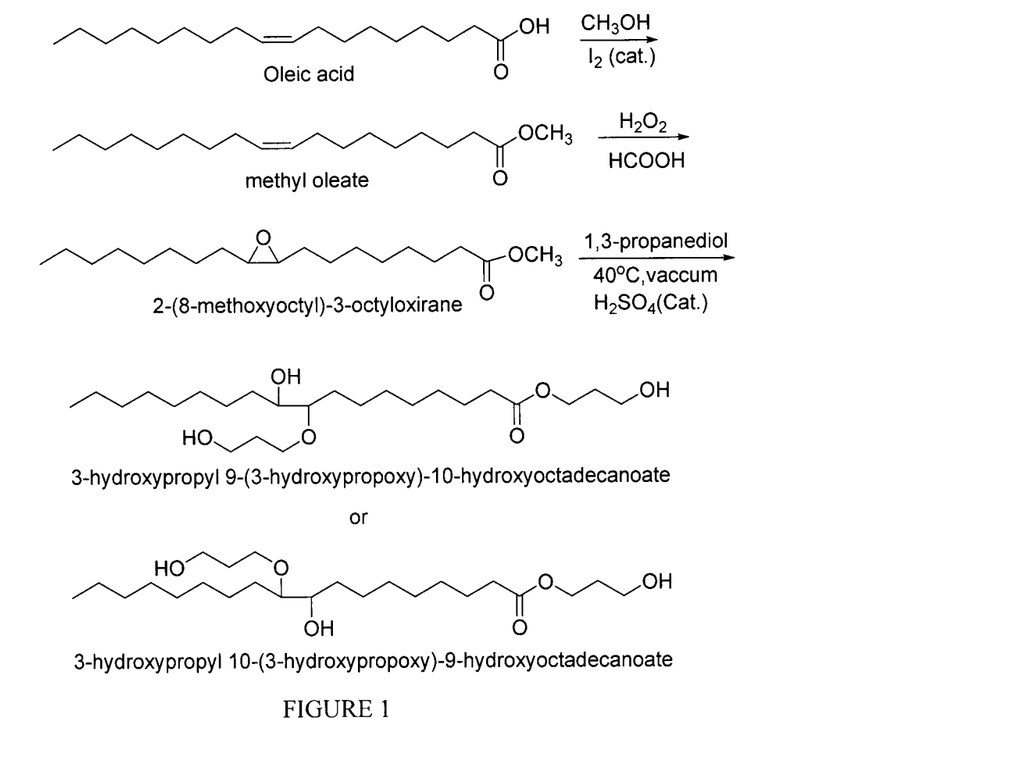
FIG. 1 shows a reaction scheme of one embodiment of the present invention, for the conversion of oleic acid to a novel oleic acid polyol.

In one aspect, the invention comprises a process for the preparation of polyols generally comprising the step of epoxidizing a fatty acid substrate which has at least one C—C double bond, followed by hydroxylation to produce the polyol. One exemplary reaction scheme is shown in FIG. 1, which is described below.

The fatty acid substrate may comprise free fatty acids, or an alkyl ester of a fatty acid, such as a methyl or ethyl ester of a fatty acid, where the fatty acid has at least one C—C double bond. In one embodiment, the fatty acid comprises oleic acid, which is a major component of many vegetable oils, or the methyl or ethyl ester of oleic acid. In one embodiment, the fatty acid substrate may comprise unsaturated triglycerides, such as found in refined or partially refined vegetable oils, such as canola oil, olive oil, sunflower oil, corn oil, soy oil, flax oil, palm oil or other naturally sourced plant oils. Unsaturated triglycerides may also be sourced from certain animal oil sources such as tallow or fish oils.

Any oil containing unsaturation (double bonds) can be used as starting material, preferably those oils with higher degrees of unsaturation such as canola oil, high oleic canola oil, sunflower oil, flaxseed oil, solin oil, yellow mustard oil, brown mustard oil and oriental mustard oil, palm oils, fractionated oils for example, palm oil olein, camelina oil. Edible oils which are fully refined, (for example, degummed, bleached, deodorised) can be used as can non-refined oils that may not be food grade, such as juvenile or "green" canola, camelina oil, high erucic acid rapeseed oil. Use of different oils with different triglyceride compositions, when fully or partially epoxidised, will result in different polyols, molecular weights (MWs), hydroxyl numbers (OH#) and viscosities giving access to a wide variety of polyols for various purposes.

Free fatty acids may be converted to alkyl esters of fatty acids using any conventional technique, which are well known to those skilled in the art. For example, the fatty acid may be refluxed with methanol and iodine, or heated in a methanolic solution of acid or base. After removal of methanol, the residue may be extracted with a suitable solvent, washed, dried and concentrated to produce a methyl ester of the fatty acid. For example, oleic acid may be converted to methyl oleate in this manner.

There are many well-known routes to produce methyl esters of fatty acids and any suitable method may be used. In embodiments using natural triglyceride oils, an esterification step is not necessary. Oleic acid is the major fatty acid in many vegetable oils and therefore the description of its conversion to a polyol permits one skilled in the art to consider the application to other fatty acids, or mono-, di- or triglycerides, or mixtures thereof. Any fatty acid may be converted to methyl esters for use in making polyols. Similarly, any preformed methyl or ethyl esters (for example as in biodiesel) could be used provided there is some degree of unsaturation. Therefore, the fatty acid substrate is intended to include all suitable fatty acids, alkyl esters thereof, and mono-, di- or tri-glycerides, which include an unsaturated carbon chain.

The final hydroxyl number of the resulting polyols will be dependent on the degree of unsaturation (number of double of bonds) in the fatty acid substrate, the extent of the epoxidation reaction and the reaction conditions and alcohols used in converting the epoxides to polyols.

In one embodiment, the epoxidation step of the fatty acid substrate involves reaction with formic acid in an oxidizing agent, such as hydrogen peroxide. Generally, the fatty acid substrate is mixed with formic acid and cooled while hydrogen peroxide is slowly added. The reaction may then proceed at room temperature with vigorous mixing until the fatty acid substrate is consumed.

In another embodiment, acid is slowly added to a well-stirred emulsion of the fatty acid substrate and hydrogen peroxide. The fatty acid substrate is mixed with hydrogen peroxide and cooled while formic acid is added slowly. The reaction may then proceed at room temperature with vigorous mixing until the fatty acid substrate is partially or wholly consumed.

In one embodiment, the epoxidation reaction may be controlled by reaction time, resulting in partial epoxidation products that can be carried forward to the subsequent ring opening step, thus controlling the final hydroxyl value of the resulting polyol. As a result, the functionality of polyols may be optimized towards specific applications. For example, the hydroxyl number values of polyols used in rigid foams is very high, whereas the hydroxyl number of polyols used in flexible foams is low. A low degree of epoxidation will result in polyols having lower hydroxyl numbers.

In one embodiment, there is no need to neutralise the acid prior to subsequent steps because remaining acid does not interfere with the following ring opening step.

In one embodiment, the epoxidized fatty acid substrate may then hydroxylated in a ring opening step with an alcohol, or mixtures of alcohols. In one embodiment, the ring opening step is performed with an alkane diol, such as 1,3 propanediol, and a mineral acid, such as sulphuric acid. Hydroxylation produces the desired polyols having available hydroxyl groups at the double bond site or sites of the fatty acid substrate, and at the carboxylic acid site. The choice of the alkane diol may be varied to produce polyols of various structures and properties. For example, the treatment of methyl oleate with 1,3 propanediol results in a mixture of 3-hydroxypropyl 9-(3-hydroxypropoxy)-10-hydroxyoctadecanoate and 3-hydroxypropyl 10-(3-hydroxypropoxy)-9-hydroxyoctadecanoate.

Suitable diols may include 1,2-propane diol, 1,3-propane diol, ethylene glycol, glycerol, glycerol acetates, or mixtures thereof, and may also include mixtures of two or more reactive alcohols, for example, mixtures of 1,2-propane diol and 1,3-propane diol, or mixtures of 1,3-propanediol and ethanol.

In one embodiment, the reactivity and physical characteristics of the polyol can be controlled by choice of diol in the ring opening step. For example, use of 1,3-propanediol affords a polyol with primary hydroxyl groups (arising from the diol) and secondary hydroxyl groups (arising from ring opening of the epoxide), whereas use of 1,2-propanediol affords a polyol with almost exclusively secondary hydroxyl groups. As is well-known in the art of polyurethane chemistry, the reactivity of isocyanates with primary hydroxyl groups is greater than with secondary hydroxyl groups. Thus, one type of polyol may suit a particular application, or polyols with primary and secondary hydroxyl groups may be blended to afford a polyol mixture that offers a tailored reactivity.

In a preferred embodiment, the use of "green" chemistry may be emphasized. Therefore, in one embodiment, the fatty acid substrate and the diol are sourced from renewable resources. The other reactants are largely non-toxic, and the reactions may be contained in readily available simple reaction vessels and under mild conditions.

In one embodiment, an organic solvent such as ethyl acetate is used to extract the esterified fatty acid and/or the epoxidized fatty acid substrate, and/or the desired polyol(s). This solvent lowers viscosity and facilitate transfers between vessels. However, in one embodiment, the process may be implemented solvent-free which would avoid the need to redistill and recycle the solvent. Extraction of the desired intermediate or polyol with a solvent may be replaced with additional washing and separation steps, such as with centrifugation.

The polyols of the present invention may be used in polymer chemistry in the same manner as known polyols. Monomeric polyols may be polymerized into polyesters or polyethers, as is well known in the art. They may be reacted with isocyanates to make polyurethanes. If the fatty acid substrate comprises triglycerides such as canola oil, the resulting polyols will be a mixture of polymeric, oligomeric, and monomeric forms. Therefore, in one aspect, the invention comprises a method of forming oligomeric and polymeric polyols directly from a fatty acid substrate.

As will be apparent to those skilled in the art, various modifications, adaptations and variations of the foregoing specific disclosure can be made without departing from the scope of the invention claimed herein.

EXAMPLES

The following examples are provided to illustrate embodiments of the invention, but should not be considered limiting of the claimed invention.

Example 1

Esterification of Oleic Acid to Make Methyl Oleate (MO)

Oleic acid (200.0 g, 354.0 mmol), methanol (200.0 ml) and iodine (2.0 g, 1.0%), were refluxed for 12 hr. The progress of the reaction was monitored by thin layer chromatography (TLC). After the reaction, excess methanol was removed under reduced pressure and the residue was extracted with ethyl acetate. The ethyl acetate was washed with a solution of sodium thiosulfate and subsequently washed the organic layer with water, NaHCO$_3$ and brine, dried over Na$_2$SO$_4$ and concentrated with rotary evaporator to give the desired methyl oleate (210.5 g).

Example 2

Structures were Identified by NMR $^1$H NMR of MO: 300 MHz, Chemical shifts in CDCl$_3$ (ppm) 5.35 (—C$\underline{H}$═C$\underline{H}$—, 2H), 3.65 (—OC$\underline{H}_3$, 3H), 2.30 (—C$\underline{H}_2$C═OOCH$_3$, 2H) (2.05, 1.65, 1.30 (—C$\underline{H}_2$—), 0.90 (—C$\underline{H}_3$)

$^1$H NMR of EMO: 300 MHz, Chemical shifts in CDCl$_3$ (ppm), 2.90 (Epoxidation part, 2H), 3.65 (—OC$\underline{H}_3$, 3H), 2.30, (Beside the Epoxidation part, 2H), 1.65, 1.50, 1.30 (—C$\underline{H}_2$—), 0.90 (—C$\underline{H}_3$)

$^1$H NMR of HEMO: 300 MHz Chemical shifts in CDCl$_3$ (ppm), 4.25 (—C═OOC$\underline{H}_2$—, 2H), 3.80, 3.70, 3.50, 3.20 (—C$\underline{H}_2$OH, 6H, —O$\underline{H}$, 1H), 0.90 (—C$\underline{H}_3$)

Example 3

Epoxidation of Methyl Oleate (EMO)

To a stirred solution of methyl oleate (MO) (200.00 g, 675 mmol) and formic acid (62.09 g, 1.35 mol) cooled in an ice bath (0° C.), H$_2$O$_2$ (30.0% in H$_2$O, 306.00 mL, 2.70 mol) was added slowly. The reaction was then allowed to proceed at room temperature with vigorous stirring until LC/MS analysis indicated that MO had been consumed (around 19 hr). The reaction was then transferred to a separatory funnel, and ethyl acetate (500 mL) was added and the lower aqueous phase was removed. The organic phase was then washed with water, NaHCO$_3$ and brine, dried with Na$_2$SO$_4$, filtered, concentrated using a rotary evaporator, and placed under vacuum until constant weight was achieved to yield epoxidized oleic acid (EMO) as a clear light yellow oil (225.0 g).

Example 4

Structures were Identified by NMR $^{13}$C NMR of EMO: 75 MHz Chemical shifts in CDCl$_3$ (ppm), 174 (—$\underline{C}$═OO—), 57 (Epoxidation parts), 51 (—O$\underline{C}$H$_3$—), from 34.0 to 23 (—$\underline{C}$H$_2$—), 14 (—$\underline{C}$H$_3$).

$^{13}$C NMR of HEMO: 75 MHz Chemical shifts in CDCl$_3$ (ppm) 174.1 (—$\underline{C}$═OO—), 83.3 (—$\underline{C}$OH), 72.8, 68.9, 61.0, 58.8, 14.0 (—$\underline{C}$H$_3$)

Example 5

Hydroxylation of Epoxidized Methyl Oleate (HEMO)

To a stirred solution of EMO (100.10 g, 0.321 mol) in 1,3-propanediol (73.28 g, 1.282 mmol) was added H$_2$SO$_4$ (Conc., 3.145 g, 10.0 mol %) and stirring continued at 40° C. under low vacuum for 20-24 hrs. After the reaction was finished, ethyl acetate (500.00 mL) was then added, and the solution was washed with water, the organic layer was washed with NaHCO$_3$ and brine then dried with anhydrous Na$_2$SO$_4$. The solution was then filtered and concentrated using a rotary evaporator to produce a clear light yellow oily product (230.0 g).

Example 6

Normal Phase LC/MS Results (Silica Column) of Oleic Acid Polyol

Figure 2:
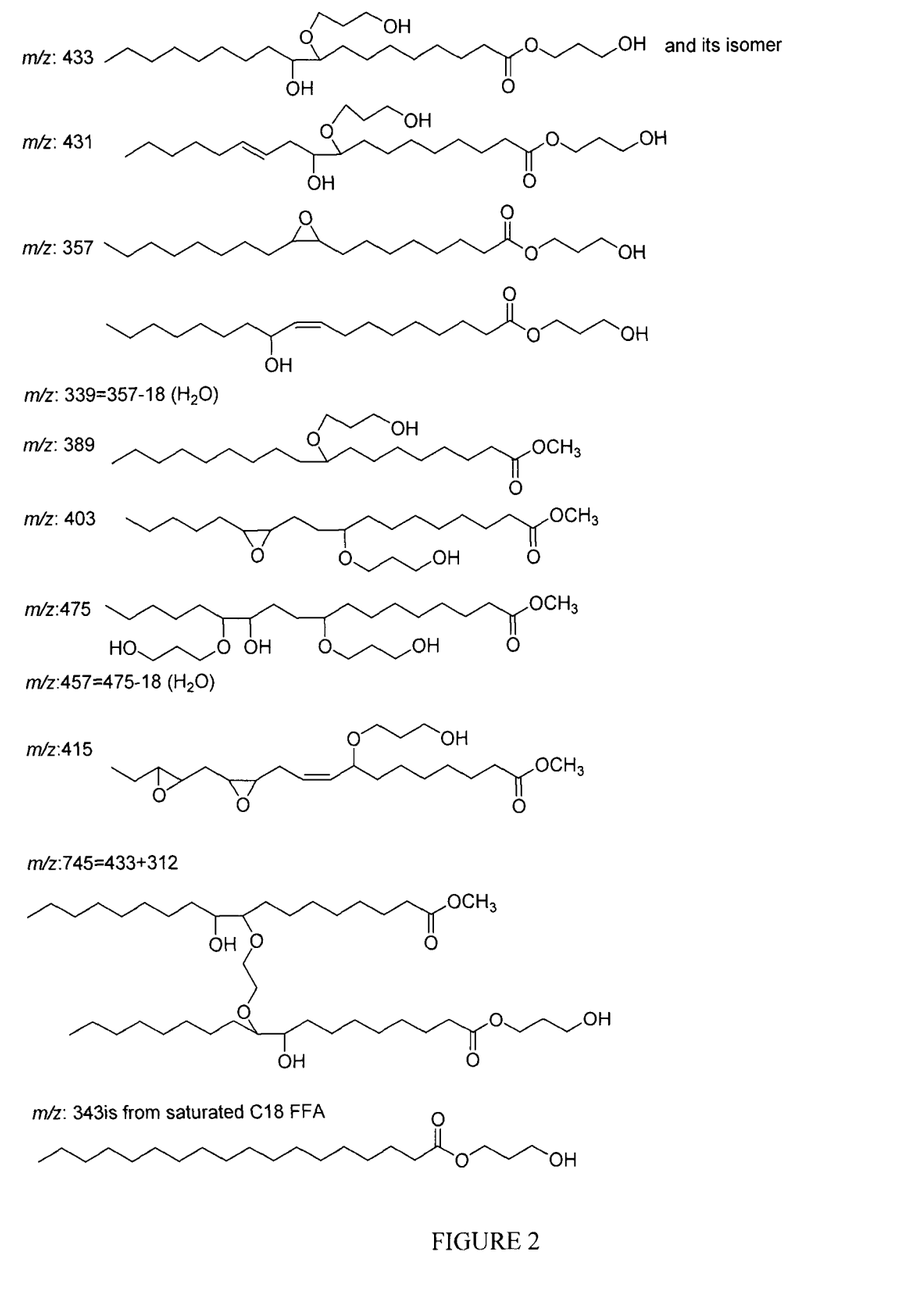
FIG. 2. Structures of oleic acid polyol characterized by LC/MS (silica column)

The important positive ions observed by mass spectrometry are shown in Table 1 with proposed structures shown in FIG. 2. The dominant ion is at m/z is 433 with structure given in FIG. 2.

TABLE 1

Molecular ion results of oleic acid polyol (OA-EP-I) obtained from LC-MS (with silica column)

| Entry | Main ions (m/z) | Other ions (m/z) |
|---|---|---|
| 1 | 433 | 353, 343, 339, 357, 389, 745, 475, 789, 415, 397, 431, |
| 2 | 433 | 355, 343, 339, 357, 389, 745, 475, 789, 431, 403 |
| Combined (1 and 2) | 433 | 343, 339, 357, 389, 745, 475, 457, 789, 415, 397, 403 |

Example 7

LC/MS (with GPC Column) Analysis of Oleic Acid Polyol

In normal phase LC/MS the maximum molecular weight component observed was around m/z 780. In order to look for high molecular weight compounds not observed due to limitations of this experiment, oleic acid polyol was tested by LC/MS using a GPC (gel permeation chromatography, also known as size exclusion) column.

Figure 3:
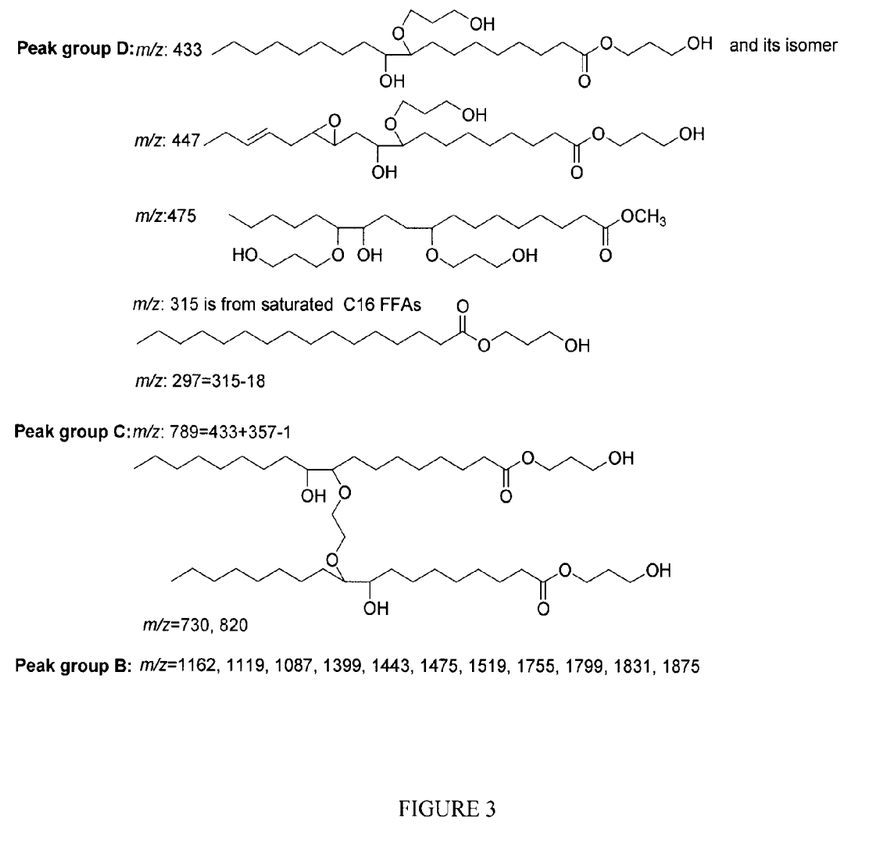
FIG. 3. Major ions observed by LC/MS (with GPC column) analysis of oleic acid polyol FIG. 4. GPC/RI Analysis of oleic acid polyol FIG. 5. Silica column LC/MS results of canola oil polyol FIG. 6. GPC/MS analysis of canola oil polyol—major ions FIG. 7. GPC/RI Analysis of Canola oil polyol

GPC/MS resulted in 3 groups of signals (3 peaks in the total ion current trace). These were labeled as B, C and D from short retention time to long retention time respectively. These peaks correspond to B, C and D seen the GPC/RI traces shown in FIG. 4 below. The proposed structures of major species are shown in FIG. 3.

Example 8

GPC/RI Analysis of Oleic Acid Polyol

Figure 4:
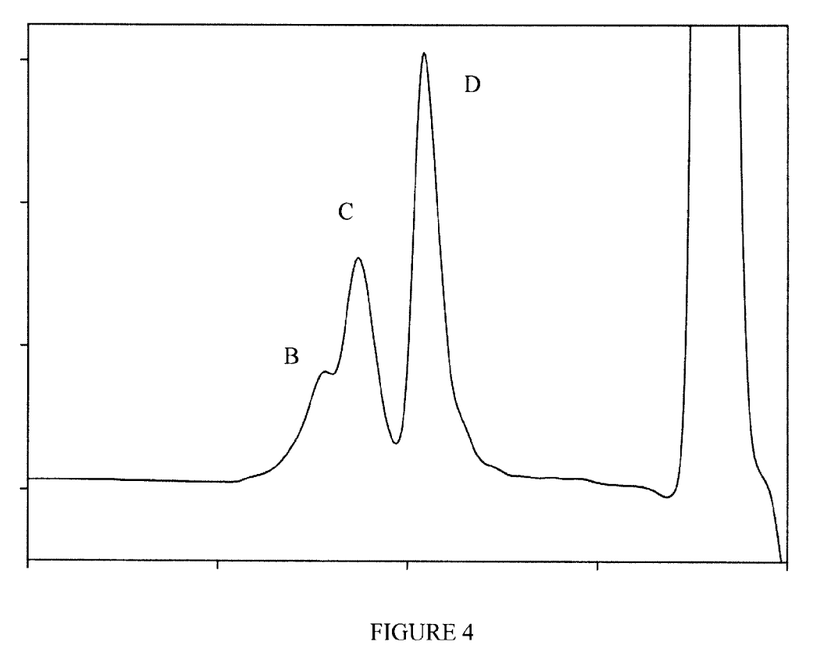

A typical GPC with refractive index detection GPC/RI chromatogram of oleic acid polyol is shown in FIG. 4. The retention times of the major peaks are shown in Table 2 along with those of standards to allow estimation of average molecular weights.

TABLE 2

Retention time of polyols and standard samples in GPC

| | Retention time (Minute) | | |
|---|---|---|---|
| Oleic acid polyol | B: 5.566 (M: ~1110) | C: 5.746 (M: ~780) | D: 6.085 (M: ~430) |
| Molecular Weight Standards | 5.584 (M: 1101) | 5.868 (M: 625) | 6.295 (M: 314) |
| Canola oil | 5.722 (M: 885) | | |
| Oleic acid | | | 6.583 (M: 284) |

The estimated molecular weights obtained by GPC/RI are consistent with those obtained by GPC/MS demonstrating that in this example the degree of oligomerisation is mainly limited to trimers and lower, although up to pentamers are observed at low abundance. Peaks D and C make up the bulk of the polyol.

Example 9

Chemical/Physical Properties of Oleic Acid Polyol

TABLE 3

Chemical/Physical properties of oleic acid polyol and mass for each batch

| Entry | Hydroxyl value (mg KOH/g) | Acid value (mg KOH/g) | Viscosity (Pa·s) at 25° C. | Mass (g) |
|---|---|---|---|---|
| 1 | 324 | 0.6 | 0.65 | 30 |
| 2 | 282 | 0.7 | 0.70 | 230 |
| 3 | 277 | 0.5 | 0.68 | 231 |
| Combined (2 & 3) | 275 | 0.6 | 0.71 | 461 |

Example 10

Epoxidation of Canola Oil (ECO)

To a stirred solution of canola oil (CO) (800.00 g, 0.904 mol) and formic acid (85%) (249.65 g, 5.42 mol) cooled in an ice bath (0° C.) was added $H_2O_2$ (~30.0% in $H_2O$, 1229.37 mL, 9.04 mol) slowly. The reaction was then allowed to proceed at room temperature with vigorous stirring until LC/MS analysis indicated that CO had been consumed (around 19 hr). After this, the reaction was transferred to a separatory funnel, ethyl acetate (2000 mL) was added and the lower aqueous phase was removed. The organic phase was then washed with water, $NaHCO_3$ and brine, dried with $Na_2SO_4$, filtered, concentrated with rotary evaporator, and placed under vacuum until weight constant to provide epoxidized canola oil (ECO) as a clear light yellow oil 860.0 g.

Example 11

Hydroxylation of Epoxidized Canola Oil (HECO)

To a stirred solution of ECO (860.00 g, 0.92 mol), 1,3-propanediol (700.12 g, 9.21 mol) and $H_2SO_4$ (Conc., 27.07 g, 10.0 mol %) was added and stirring continued at 60° C. under low vacuum (10 mmHg) for 46-48 hours. After this the reaction was complete and ethyl acetate (2000.00 mL) was added. The solution was washed with water then the organic layer was washed with $NaHCO_3$ and brine, dried with anhydrous $Na_2SO_4$, filtered and finally concentrated using a rotary evaporator. This produced 927.0 g of a red transparent oily product.

Example 12

Normal Phase-LC/MS Analysis of Canola Oil Polyol

Figure 5:
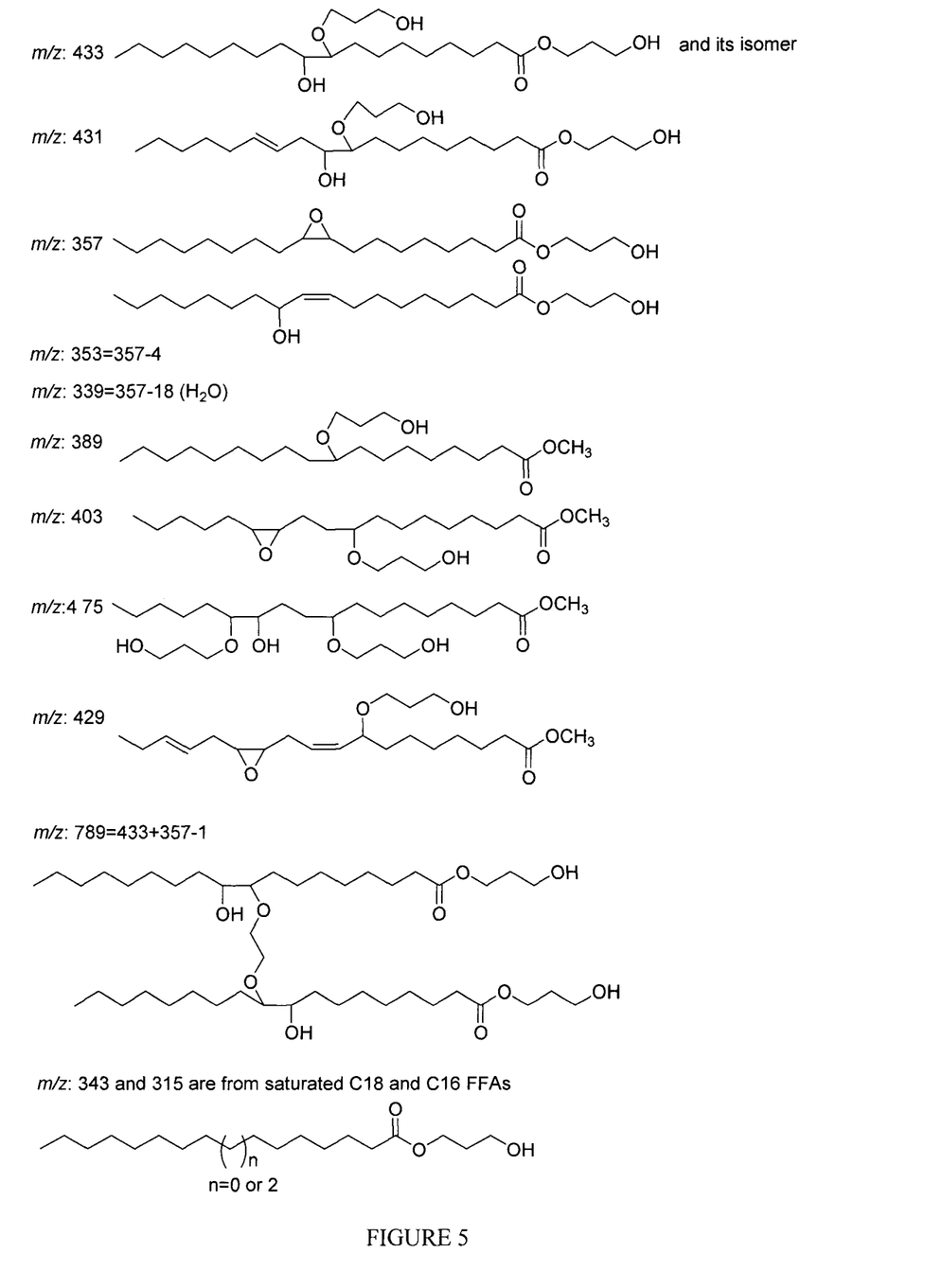

LC/MS analysis was conducted under normal phase conditions using a silica column. Results for canola oil polyol are shown in Table 4, and the suggested structures of the major ions observed are listed in FIG. 5. The structure given for the ion at m/z 433 ($MH^+$) is the major product from oleic acid.

TABLE 4

LC/MS (silica column) ions observed in each sample

| Entry | Main ions ($MH^+$) | Other ions ($MH^+$) |
|---|---|---|
| 1 | 433 | 343, 315, 339, 357, 475, 389, 789, 403 |
| 2 | 433 | 429, 343, 315, 297, 339, 357, 475, 389, 789, 431, 403 |
| 3 | 433 | 325, 343, 315, 297, 339, 789, 353, 335 |
| 4 | 433 | 343, 315, 297, 339, 357, 475, 389, 789 |
| 5 | 433 | 429, 343, 315, 297, 339, 357, 475, 389, 789, 431, 353 |
| 6 | 433 | 429, 343, 315, 339, 357, 475, 389, 789, 431, 403 |
| mixture of entries 1-6 | 433 | 429, 343, 315, 339, 357, 475, 389, 789, 403 |

Example 13

LC/MS (with GPC Column) Analysis of Canola Oil Polyol

Figure 6:
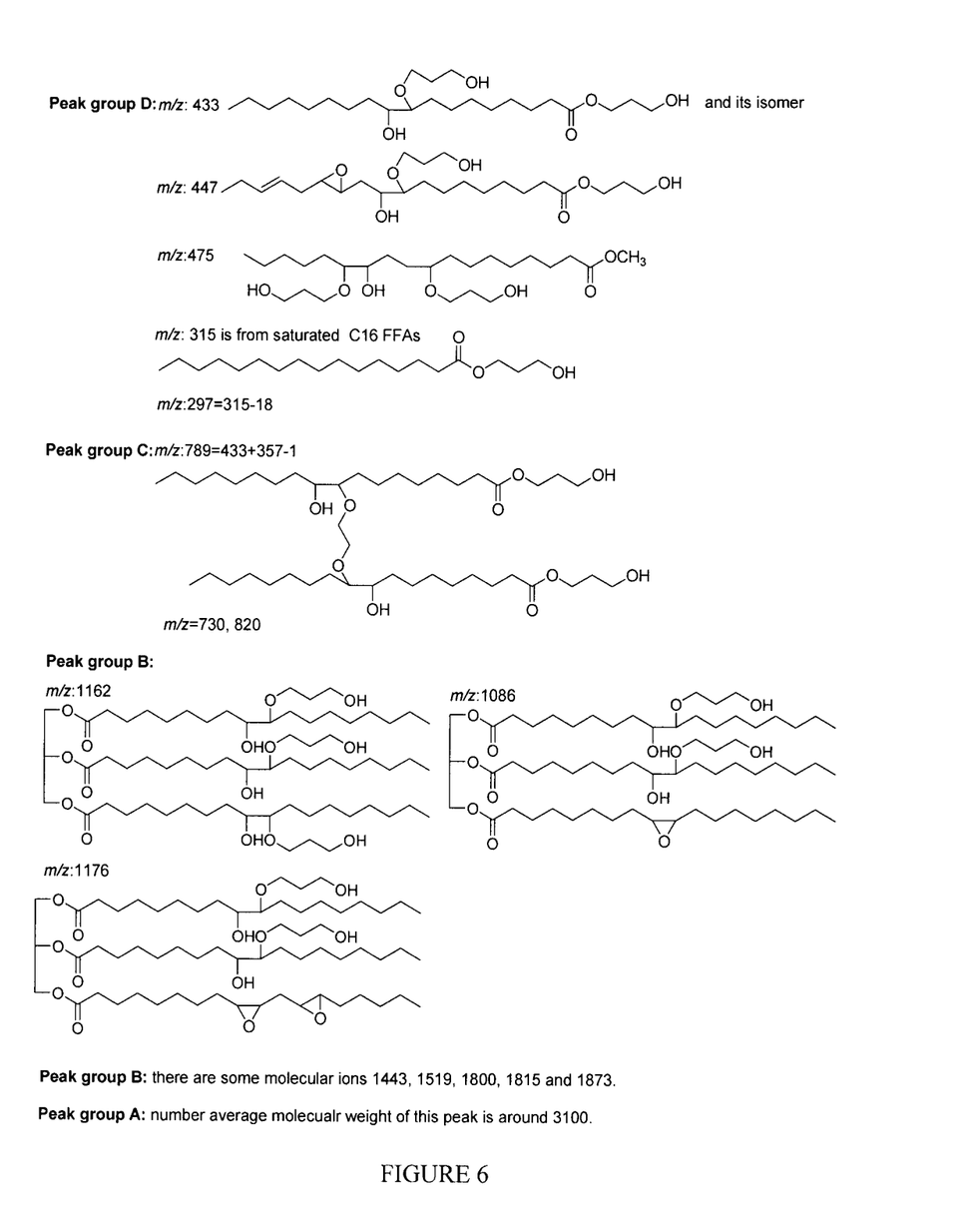
Figure 7:
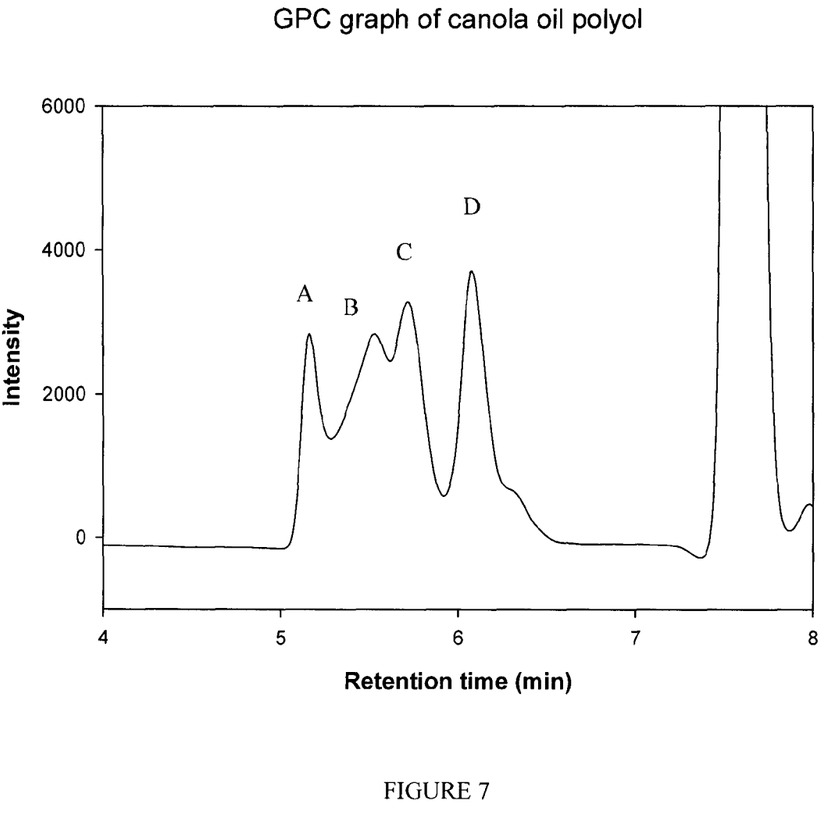

The highest molecular weight component found by LC/MS using the normal phase silica column was around m/z 780. To look for high molecular weight components, canola oil polyol was tested by LC/MS using a GPC column. Results and the suggested structures of the major ions observed are given in FIG. 6. 4 groups of signals were observed which were labeled A, B, C and D from shortest to longest retention time as indicated in FIG. 7.

The average molecular weight of the component Group A is around 3100 g/mol. The ions shown for other groups are examples of the major components—other ions are observed.

Example 14

Analysis of Canola Polyol by GPC with Refractive Index Detection

A GPC chromatogram of canola oil polyol is shown in FIG. 7 and the retention times of each signal are shown in Table 5.

TABLE 5

Retention times for canola oil polyol and standard samples by GPC-RI

| | Retention time (Minute) | | | |
|---|---|---|---|---|
| Canola oil polyol | A: 5.16 | B: 5.50 | C: 5.72 | D: 6.08 |
| Molecular Weight | | 5.58 | 5.87 | 6.30 |
| Standards | | (M: 1101) | (M: 625) | (M: 314) |
| Canola oil | | 5.72 | | |
| | | (M: 885) | | |
| Oleic acid | | | | 6.58 |
| | | | | (M: 284) |

Example 15

Chemical/Physical Properties of Canola Oil Polyol

Chemical/physical properties measured for canola oil polyol are listed in Table 6 (200 g scale) and Table 7 (800 g scale).

TABLE 6

Summary of chemical/physical properties of canola polyol produced at 200 g scale

| entry | Hydroxyl value (mg KOH/g) | Acidity value (mg KOH/g) | Viscosity (Pa · s) at 25° C. |
|---|---|---|---|
| 1 | 270.0 | 1.2 | 1.61 |
| 2 | 240.0 | 1.2 | 3.94 |
| 3 | 259.0 | 0.2 | 3.58 |
| 4 | 258.0 | 1.2 | 5.11 |
| 5 | 261.0 | 1.2 | 2.10 |
| 6 | 264.0 | 0.6 | 2.10 |
| mixture of entries 1-6 | 258.2 | 1.1 | 2.67 |

TABLE 7

Summary of chemical/physical properties of canola polyol produced at 800 g scale (C-EP-I)

| entry | Hydroxyl value (mg KOH/g) | Acidity value (mg KOH/g) | Viscosity (Pa · s) at 25° C. |
|---|---|---|---|
| 1 | 264 | 2.4 | 2.90 |
| 2 | 251 | 1.7 | 2.96 |
| 3 | 266 | 0.9 | 2.72 |
| 4 | 274 | 0.8 | 2.80 |
| mixture of entries 1-4 | 264 | 1.5 | 3.07 |

Example 16

Polyols from Different Vegetable Oils

The following polyols were produce based on the methods described above in relation to epoxidized canola oil and 1,3-propane diol. The physical properties of these polyols are listed in Table 8.

TABLE 8

Physical properties of polyols made from 12 different vegetable oils

| Entry | Hydroxyl number (mgKOH/g) | Viscosity |
|---|---|---|
| High oleic canola oil | 244 | 4.5 |
| Sunflower oil | 286 | 3.3 |
| Juvenile canola oil | 262 | 5.8 |
| flax | 292 | 4.2 |
| Camelina | 272 | 4.7 |
| Oriental mustard | 247 | 5.7 |
| Brown mustard | 246 | 4.8 |
| Yellow mustard | 218 | 12.8 |
| Palm oil olein (RBD) | 124 | 1.5 |
| Palm oil (RBDPO) | 86 | 1.4 |

Example 17

Altering Hydroxyl Number

In order to make low OH# polyol for making flexible foam, 3 batches of reactions were tried to make polyol from ECO and mixtures of ethanol and 1,3-propanediol with different molar ratios. The polyols obtained from the different alcohol ratios are listed in Table 9.

TABLE 9

Physical properties of polyols made from ECO mixture ethanol and 1,3-propanediol (with different molar ratios)

| Entry | Molar ratio of ECO/Ethanol/1,3-propanediol | Hydroxyl number (mgKOH/g) | Viscosity Pa · s@ 25° C. |
|---|---|---|---|
| 1 | 1/8/2 | 172 | 0.20 |
| 2 | 1/6/4 | 190 | 0.35 |
| 3 | 1/2/8 | 217 | 3.30 |

As may be seen, increasing the monoalcohol proportion to the diol resulted in a significant decrease in hydroxyl number, and a dramatic decrease in viscosity.

Example 16

Incomplete Epoxidation

Canola oil was epoxidized in accordance with Example 10, but the epoxidation step was stopped prior to complete consumption of the canola oil. The resulting partially epoxidized canola oil was converted to polyol with reduced hydroxyl number. Physical properties of the polyols are listed in Table 10.

TABLE 10

Partially epoxidized of canola oil and physical properties of corresponding polyols

| Partially epoxidized canola oil | Epoxidation time (hour) | Polyol Hydroxyl number (mgKOH/g) | Polyol Viscosity Pa·s@ 25° C. |
|---|---|---|---|
| A | 2 hr | 71 | 0.35 |
| B | 3 hr | 92 | 0.79 |
| C | 4 hr | 124 | 2.26 |
| D | 5 hr | 145 | 6.4 |
| E | 6 hr | 142 | 10.9 |

As can be seen a lower epoxidation time correlates to a lower hydroxyl number and a lower viscosity.

The invention claimed is:

1. A method for the preparation of polyols from an unsaturated fatty acid substrate having at least one C—C double bond, comprising the steps of:
   (a) epoxidizing the unsaturated fatty acid substrate with an acid and an oxidizing agent to obtain an epoxidized fatty acid substrate; and
   (b) hydroxylating the epoxidized fatty acid substrate with an alkane diol and a mineral acid to obtain a polyol.

2. The method of claim 1, wherein the epoxidized fatty acid substrate is hydroxylated with two or more reactive alcohols, at least one of which is a propane diol, to produce a blend of polyols having a desired average molecular weight, viscosity or hydroxyl number.

3. The method of claim 1 further comprising the step of forming an alkyl ester of the fatty acid substrate prior to the epoxidation step.

4. The method of claim 1, wherein the unsaturated fatty acid substrate comprises triglycerides and the resulting polyol blend comprises oligomeric and polymeric polyols.

5. The method of claim 4 wherein the unsaturated fatty acid substrate comprises canola oil, high oleic canola oil, sunflower oil, juvenile canola oil, flax oil, camelina oil, solin oil, yellow mustard oil, brown mustard oil, oriental mustard oil, palm oil olein or palm oil, soy oil, high erucic acid rapeseed oil, distillers corn oil, carinata or mixtures thereof.

6. The method of claim 1 wherein the epoxidation step is stopped prior to complete epoxidation of the unsaturated fatty acid substrate, resulting in a blend of polyols having a lower viscosity or lower average molecular weight.

7. The method of claim 1 wherein the alkane diol comprises 1,2 propanediol, 1,3 propanediol, or mixtures thereof.

8. The method of claim 7 wherein the alkane diol comprises a mixture of 1,2 propanediol and 1,3 propanediol, and the ratio of 1,2 propanediol to 1,3 propanediol is controlled to produce a blend of polyols with desired properties.

9. The method of claim 8 wherein the desired property is a greater number of primary hydroxyl groups which is achieved by using relatively more 1,3 propanediol.

10. The method of claim 8 wherein the desired property is a greater number of secondary hydroxyl groups which is achieved by using relatively more 1,2 propanediol.

11. The method of claim 2 wherein one reactive alcohol comprises ethanol.

12. The method of claim 11 wherein the ratio of ethanol to propane diol is controlled to produce a blend of polyols having greater viscosity or greater hydroxyl number as the relative amount of ethanol decreases.

13. The method of claim 1 wherein the unsaturated fatty acid substrate comprises a fatty acid, an alkyl ester of a fatty acid, a mono-, di- or triglyceride, or mixtures thereof.

14. The method of claim 13 wherein the unsaturated fatty acid substrate is blended from different unsaturated fatty acid substrates in order to produce a blend of polyols having a desired property.

15. The method of claim 1 wherein the mineral acid comprises sulphuric acid.

16. The method of claim 1 implemented as solvent-free.

17. The method of claim 1 comprising the use of a solvent to extract either or both of the epoxidized fatty acid substrate and the polyol.

18. The method of claim 1 wherein the hydroxylation step is taken at 40° C. to 60° C., for 20 to 48 hours.

* * * * *